United States Patent
Torrie et al.

(10) Patent No.: US 10,531,892 B2
(45) Date of Patent: Jan. 14, 2020

(54) SURGICAL NEEDLE

(71) Applicant: Smith & Nephew, Inc., Andover, MA (US)

(72) Inventors: Paul Alexander Torrie, Marblehead, MA (US); Jennifer Stambek, Valencia, CA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/801,578

(22) Filed: Mar. 13, 2013

(65) Prior Publication Data

US 2013/0267980 A1    Oct. 10, 2013

Related U.S. Application Data

(60) Provisional application No. 61/610,177, filed on Mar. 13, 2012.

(51) Int. Cl.
*A61B 17/34* (2006.01)
*A61B 17/00* (2006.01)

(52) U.S. Cl.
CPC ...... *A61B 17/3403* (2013.01); *A61B 17/3496* (2013.01); *A61B 17/3474* (2013.01);
(Continued)

(58) Field of Classification Search
CPC ........ A61B 2017/3405; A61B 13/3494; A61B 1/34947; A61B 17/3403; A61B 17/3474;
(Continued)

(56) References Cited

U.S. PATENT DOCUMENTS 1,527,291 A    7/1923    Zorraquin
2,623,521 A *  12/1952   Shaw ..................... 604/170.02
(Continued)

FOREIGN PATENT DOCUMENTS

CN    2553748 A    6/2003
CN    101730506 A  6/2010
(Continued)

OTHER PUBLICATIONS

International Search Report for PCT/US2014/028504 dated Jul. 21, 2014.
(Continued)

*Primary Examiner* — Diane D Yabut
*Assistant Examiner* — Majid Jamialahmadi
(74) *Attorney, Agent, or Firm* — Burns & Levinson, LLP; Joseph M. Maraia

(57) ABSTRACT

The disclosure provides examples of a surgical needle for entering a joint space through tissue, such as the hip joint. The surgical needle includes a stylet movable within a hollow body. The hollow body has at one end, a tip of a bevel for cutting tissue and at another end, a feedback member providing a surgeon with tactile feedback. The stylet has at one end, a resistance reducing member that when positioned a preset distance from the bevel reduces the resistance of the surgical needle through tissue. At the other end of the stylet is a stylet hub. In some examples of the surgical needle, the stylet hub includes a proximal stop, stylet locking member and/or locking member. The surgical needle advantageously provides tactile feedback, reduces resistance, and minimizes or prevents damage to delicate structures.

8 Claims, 27 Drawing Sheets

(52) U.S. Cl.
CPC ............. *A61B 2017/00424* (2013.01); *A61B 2017/00455* (2013.01)

(58) Field of Classification Search
CPC ...... A61B 17/3496; A61B 2017/00424; A61B 2017/00455; A61B 2017/00446; A61B 2017/061; A61B 17/3494; A61B 17/06109; A61B 17/06066; A61B 2090/062; A61B 2017/00451; A61B 2017/0042; A61B 2017/00429; A61B 2017/00433; A61B 17/06
USPC ......... 604/117, 164.01, 164.07, 158, 170.01, 604/170.02, 274; 606/86, 86 R, 181–183, 606/185–188
See application file for complete search history.

(56) References Cited

U.S. PATENT DOCUMENTS

| | | | |
|---|---|---|---|
| 5,104,381 A * | 4/1992 | Gresl et al. | 604/158 |
| 5,137,509 A | 8/1992 | Freitas | |
| 5,320,608 A * | 6/1994 | Gerrone | 604/117 |
| 5,401,247 A | 3/1995 | Yoon | |
| 5,509,910 A | 4/1996 | Lunn | |
| 5,569,288 A * | 10/1996 | Yoon | 606/185 |
| 5,573,511 A | 11/1996 | Yoon | |
| 5,578,053 A | 11/1996 | Yoon | |
| D379,515 S * | 5/1997 | Kuehn et al. | D24/146 |
| 6,001,084 A | 12/1999 | Rick et al. | |
| 6,071,292 A | 6/2000 | Makower et al. | |
| 6,270,484 B1 | 8/2001 | Yoon | |
| 6,656,160 B1 * | 12/2003 | Taylor et al. | 604/158 |
| 6,837,878 B2 * | 1/2005 | Smutney et al. | 604/272 |
| 8,202,251 B2 * | 6/2012 | Bierman et al. | 604/164.13 |
| 2002/0099335 A1 | 7/2002 | Zohmann | |
| 2003/0220677 A1 | 11/2003 | Doan et al. | |
| 2004/0133124 A1 | 7/2004 | Bates et al. | |
| 2004/0171986 A1 | 9/2004 | Tremaglio, Jr. et al. | |
| 2004/0225180 A1 * | 11/2004 | Junger | A61B 17/435 600/33 |
| 2005/0159762 A1 | 7/2005 | Nuutinen | |
| 2006/0004378 A1 * | 1/2006 | Raines, Jr. | A61B 17/562 606/99 |
| 2006/0089609 A1 | 4/2006 | Bleich et al. | |
| 2008/0188928 A1 | 8/2008 | Salahieh et al. | |
| 2009/0157099 A1 | 6/2009 | Surti | |
| 2009/0163934 A1 | 6/2009 | Raschdorf et al. | |
| 2009/0275970 A1 * | 11/2009 | Leibowitz | A61B 17/3496 606/185 |
| 2009/0287236 A1 | 11/2009 | Bakos et al. | |
| 2009/0299400 A1 * | 12/2009 | Wayman et al. | 606/185 |
| 2010/0036361 A1 | 2/2010 | Nguyen et al. | |
| 2010/0113873 A1 | 5/2010 | Suzuki et al. | |
| 2010/0160731 A1 | 6/2010 | Glovannini et al. | |
| 2010/0249750 A1 | 9/2010 | Racz | |
| 2011/0082538 A1 | 4/2011 | Dahlgren et al. | |
| 2011/0218485 A1 | 9/2011 | Tran et al. | |
| 2011/0224742 A1 | 9/2011 | Weisel et al. | |
| 2011/0257581 A1 * | 10/2011 | Koziczynski | A61B 17/06 604/11 |
| 2013/0211427 A1 | 8/2013 | Castell | |

FOREIGN PATENT DOCUMENTS

| | | | |
|---|---|---|---|
| EP | 2149339 A2 | 1/2010 | |
| EP | 2277457 A1 | 1/2011 | |
| GB | 2064963 A | 6/1981 | |
| GB | 2397235 | 7/2004 | |
| JP | S56-101305 U | 8/1981 | |
| JP | H08-511711 A | 12/1996 | |
| JP | H09-103433 A | 4/1997 | |
| JP | 2012179087 A | 9/2012 | |
| JP | 2013013592 A | 1/2013 | |
| SU | 1232236 A1 | 5/1986 | |
| SU | 1303149 A1 | 4/1987 | |
| SU | 1560143 A1 | 4/1990 | |
| WO | 9406681 A3 | 11/1994 | |
| WO | 95/00189 | 1/1995 | |
| WO | 01069838 A1 | 2/2001 | |
| WO | WO 2009/114833 * | 9/2009 | A61M 5/06 |
| WO | 2012006161 A2 | 1/2012 | |
| WO | 2012096816 A1 | 7/2012 | |

OTHER PUBLICATIONS

International Search and Written Opinion for PCT/US2013/030950 dated Sep. 16, 2013.
Written Opinion for PCT/US2014/028504 dated Jul. 21, 2014.
First Office Action and Search Report from related Chinese Application No. 2013800250782 dated Jun. 2, 2016.
Office Action from related Japanese Application No. 2015-500561 dated Dec. 19, 2016.
Office Action from related Chinese Application No. 201380025078.2 dated Feb. 7, 2017.
Office Action from related Russian Application No. 2014136479/14(059050) dated Dec. 27, 2016.
International Preliminary Report on Patentability from related PCT Application No. PCT/US2016/018234 dated Aug. 22, 2017.
Russian Office Action dated Mar. 23, 2017 for Application No. RU 2014136479.
Japanese Office Action dated Jun. 12, 2017 for Application No. JP 2015-500561.
Australian Office Action from corresponding International Application No. 2014227806, dated Dec. 11, 2017.
Japanese Application No. 2016-502808 Notice of Reasons for Rejection dated Mar. 1, 2018.

\* cited by examiner

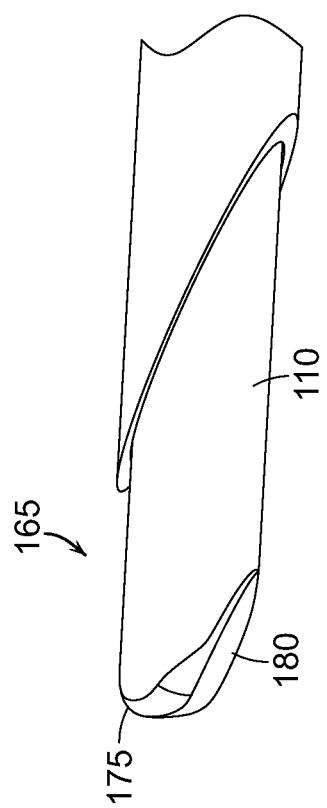

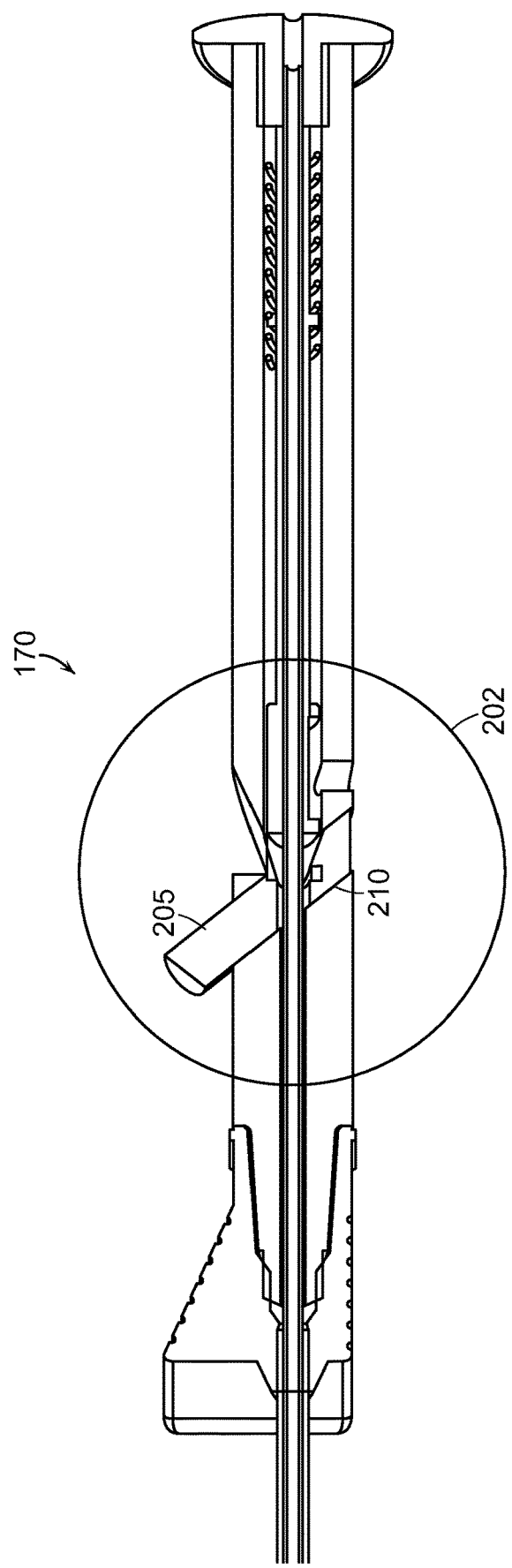

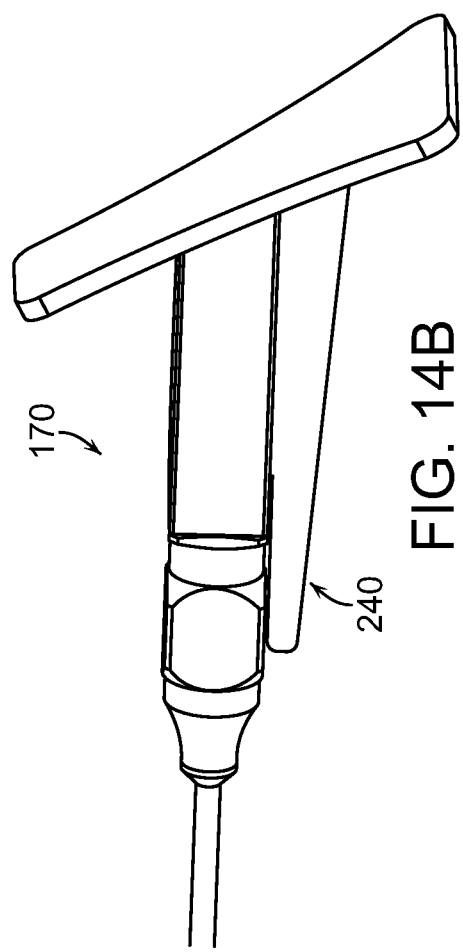

SURGICAL NEEDLE

CROSS-REFERENCE TO RELATED APPLICATIONS

This application claims priority to U.S. Patent Application Ser. No. 61/610,177, filed on Mar. 13, 2012, the disclosure of which is incorporated herein by reference in its entirety.

BACKGROUND

Arthroscopic surgery is a minimally invasive surgical procedure in which examination and treatment of damage to the interior of a joint is performed using an arthroscope, a type of endoscope that is inserted into the joint through a small incision. To accesses the interior of the joint, the surgeon inserts arthroscopic portals or cannulas through the patient's skin and through intervening layers of tissue and ligaments. The surgeon then introduces arthroscopic instruments through these access portals to perform the surgery. Creating access portal can be extremely challenging for the surgeon.

SUMMARY

Creating access portals in hip arthroscopy, especially the first portal can be problematic. The surgeon carries out the first portal blind under 2D fluoroscopic imaging with no direct visualization through an arthroscope. Studies show that a majority of iatrogenic damage is created in the femoral head by the initial blind needle placement. Other problems arise from some of the hip structures, such as the articular cartilage on the femoral head, which is quite delicate. The surgeon must be careful when forming the access portal so as to not to these structures.

The capsule surrounding the hip joint is of particular concern. The capsule is leather-like being significantly denser and "tougher" than tissue externally surrounding the capsule. Even with a sharp needle, the surgeon must push hard to pierce the capsule. However, the capsule is thin so the surgeon risks popping through the capsule, uncontrollably, and accidently damaging tissue beyond the capsule.

In view of the problems described above, there is a need to minimize the damage created by blind placement of the needle. More specifically, there is a need to control the penetration of the periarticular soft tissues and hip capsule by a needle without visual aid. These needs are addressed by a surgical needle with a blunt stylet within the needle. The blunt stylet rapidly extends beyond a tip of a bevel of the surgical needle when the surgical needle does not have tissue pressing against its distal end. For example, the blunt stylet extends just after the surgical needle exits the capsule but before contacting the femoral head.

Accordingly, in one aspect, the present disclosure relates to a surgical needle for entering a joint space through tissue. The surgical needle includes a bevel disposed at the distal end of the hollow body and a tip at the distal most end of the bevel. The surgical needle further includes a feedback member coupled to the proximal end of the hollow body. The feedback member provides a user with tactile feedback of the surgical needle moving relative to the tissue. The surgical needle further includes a passageway within the feedback member and is defined by an opening at one end of the feedback member. The passageway is in communication with the interior of the hollow tube. The surgical needle further includes a stylet having a distal end and proximal end. The stylet is movable within the hollow body between an extended position and retracted position. The surgical needle further includes a resistance reducing member disposed at the distal end of the stylet. The resistance reducing member being forward of the tip of the bevel when the stylet is in the extended position. The resistance reducing member being located at a predetermined position relative to the bevel of the hollow body when the stylet is in the retracted position. The surgical needle further includes a stylet hub disposed at the proximal end of the stylet. The stylet hub together with the passageway and opening of the feedback member couple the stylet and hollow body together.

In another aspect, the present disclosure relates to a method for entering a joint space through tissue with the foregoing surgical needle. The method includes inserting the surgical needle into tissue and advancing the surgical needle through the tissue. The resistance reducing member moves the preset distance behind the bevel of the hollow body in response to a tissue force pushing against the resistance reducing member. The method further includes rotating the surgical needle relative to the tissue and joint space in response to indications of the rotational orientation of the bevel. The indications being provided by the asymmetrical shape of the feedback member.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The foregoing and other objects, features, and advantages will be apparent from the following more particular description of the examples as illustrated in the accompanying drawings in which like reference characters refer to the same parts throughout the different views. The drawings are not necessarily to scale, emphasis instead being placed upon illustrating the principles, characteristics, and features of the examples. In the drawings:

FIGS. 9A and 9B are close up views of an example of the resistance reducing member at the distal end of the stylet.

FIGS. 13A-C are views of examples of the stylet hub with a stylet locking member.

FIGS. 14A and 14B are close up views of various manual means for unlocking a locked stylet.

DETAILED DESCRIPTION

The following description of examples is in no way intended to limit the disclosure, its application, or uses.

Figure 1:
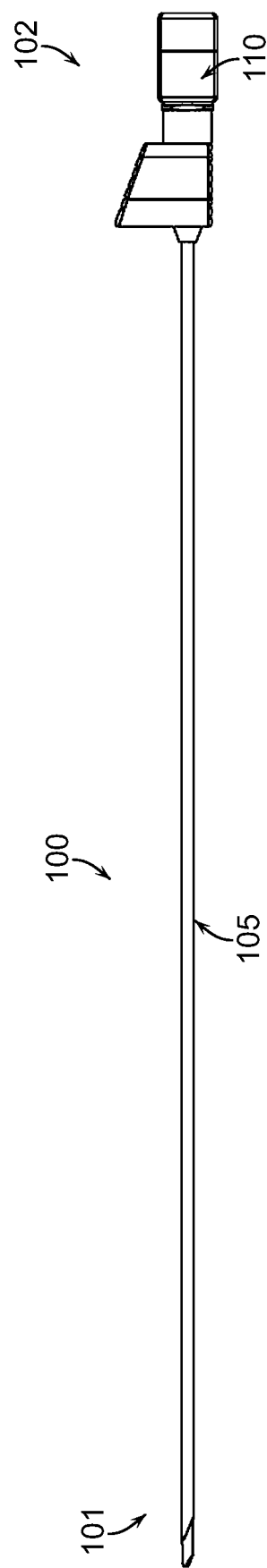
FIG. 1 is a side view of an example surgical needle having a hollow body and stylet.
Figure 2:
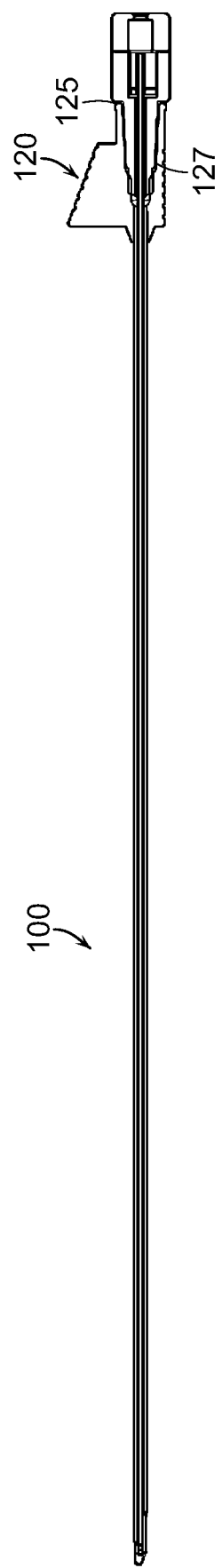
FIG. 2 is a cross-sectional view of the example surgical needle of FIG. 1.

FIGS. 1 and 2 show an example surgical needle 100 for creating portals for joint arthroscopy through which an arthroscopy and/or surgical instruments enter. The surgeon inserts the surgical needle 100 into, for example, the patient's hip joint. This can be done blind without direct visualization by the surgeon. The surgical needle 100 has a distal end 101 that is inserted into the patient and a proximal end 102 that is manipulated by the surgeon to move and rotate the surgical needle 100. The surgical needle 100 has a hollow body 105 and stylet 110 within the hollow body 105 (best seen in FIG. 2). As the surgeon moves the surgical needle 100, the stylet 110 moves between a retracted position, extended position, and positions in between (described in greater detail below).

Figure 3:
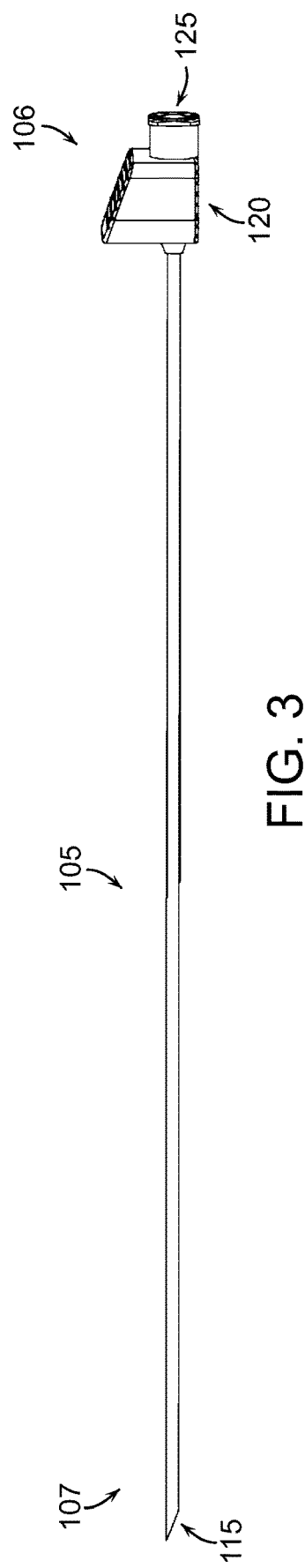
FIG. 3 is a side view of an example of the hollow body.

FIG. 3 shows an example of the hollow body 105. The hollow body 105 has a proximal end 106 and distal end 107. Disposed at the proximal end 106 of the hollow body 105 is a feedback member 120 that provides the surgeon with tactile feedback. The surgeon, in turn, is able to feel what the surgical needle 100 is doing. The feedback member 120 has an opening 125 at an end opposite the hollow body 105. The opening 125 defines a passageway 127 inside of the feedback member 120 (best seen in FIG. 2). The passageway 127 is in communication with the interior of the hollow body 105. The passageway 127 and the interior define a continuous volume that is opened at a bevel 115 at the distal end 101 of the surgical needle 100 and at the opening 125 at the proximal end 102 of the surgical needle 100. In some examples of the surgical needle 100, the opening 125 and passageway 127 are used to couple the hollow body 105 and stylet 110 together (described in greater detail below.

Figure 4:
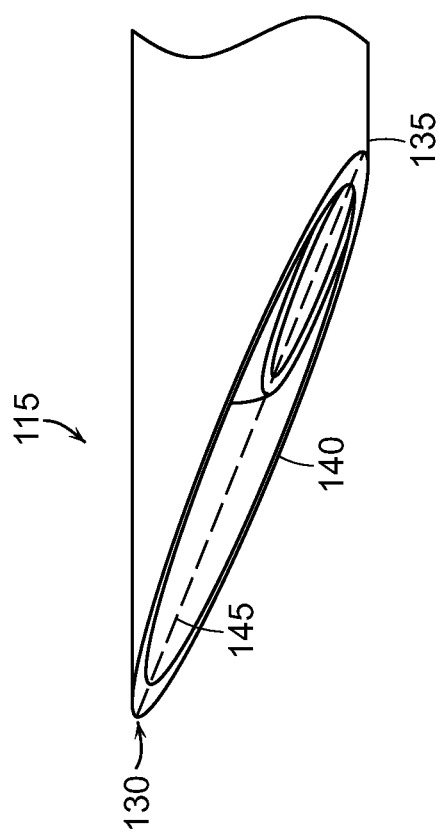
FIG. 4 is a close up view of an example of a bevel at the distal end of the hollow body.

FIG. 4 shows an example of the bevel 115 at the distal end 107 of the hollow body 105. The bevel 115 includes at the most distal end, a tip 130 for cutting/penetrating tissue and at the most proximal end, a heel 135. The tip 130 and heel 135 form a line 145 called the "leading edge" of the bevel 115. (The significance of the leading edge 145 is described later.) A bevel face or simply face 140 extends between the tip 130 and heel 135. The face 140 supports the tip 130. The face 140 may or may not be configured to cut/penetrate tissue. Furthermore, a portion of the face 140 may cut/penetrate tissue while another portion may not.

With the stylet 110 in the retracted position, the tip 130 is the first to encounter the tissue and then the face 140. As the surgeon pushes the surgical needle 100 through the tissue, more of the face 140 encounters the tissue and the resistance through the tissue increases. The surgeon feels this increase in resistance through the surgical needle 100 and pushes the surgical needle 100 harder.

As the surgeon moves the surgical needle 100 through tissue, the surgeon feels different levels of resistance. For example, the resistance felt by the surgeon when the surgical needle 100 enters the tissue is different than the resistance felt by the surgeon when the surgical needle 100 exits the tissue. In this way, the surgeon can determine the progress of the surgical needle 100 by the tactile feedback provided (transmitted) by the surgical needle 100.

Figure 5:
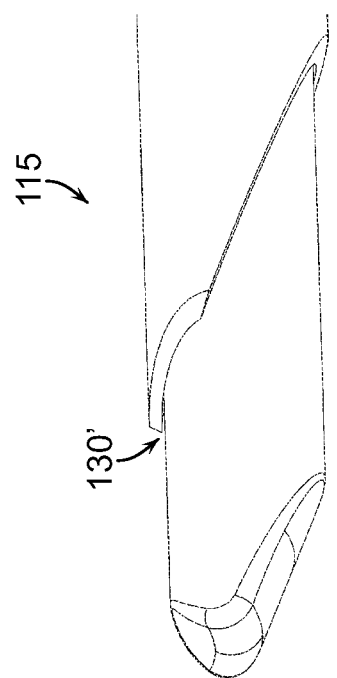
FIG. 5 is a close up view of another example of the bevel at the distal end of the hollow body with the resistance reducing member extended.

FIG. 5 shows another example of the bevel 115 at the distal end 107 of the hollow body 105. The bevel 115 includes at the distal most end, a non-catching tip 130'. The non-catching tip 130' has a profile (as shown in FIG. 5) that does not grab soft tissue when advanced.

Figure 6:
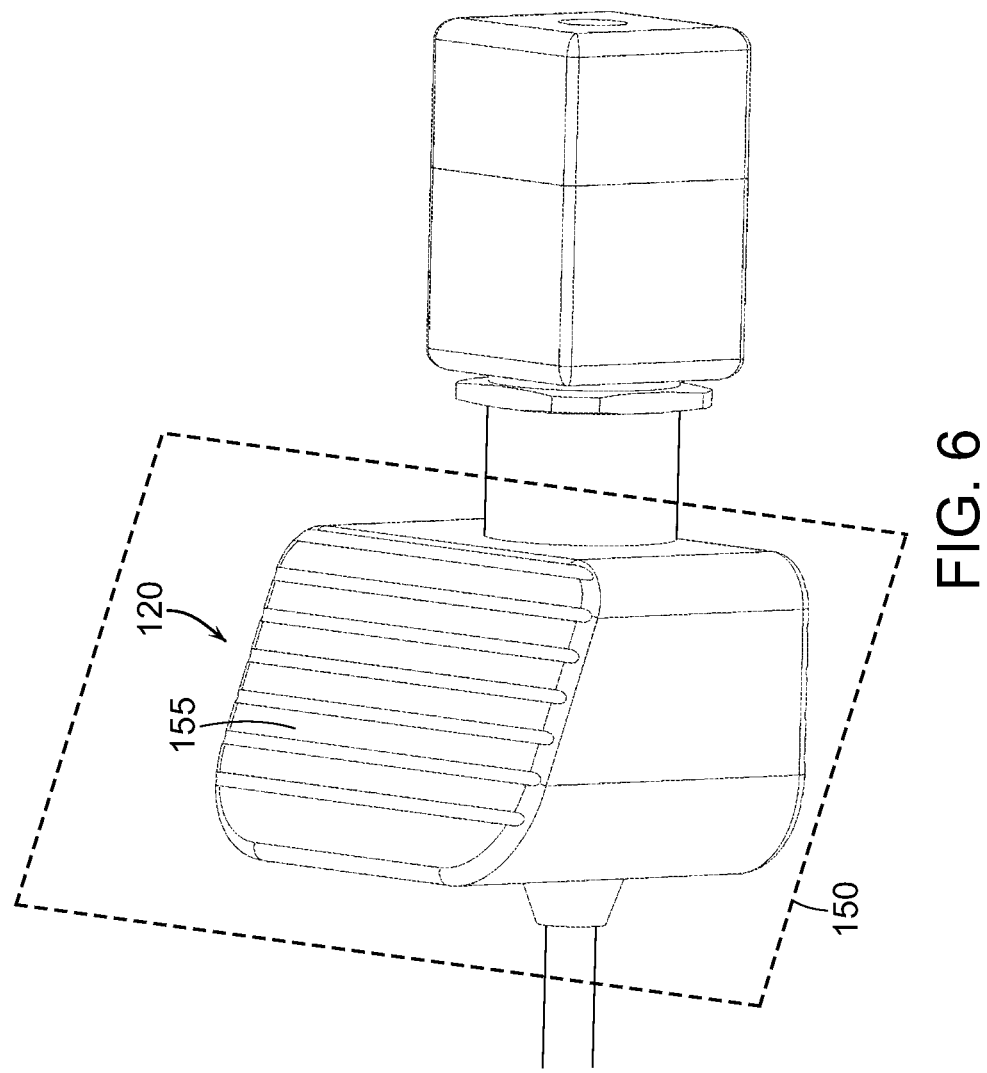
FIG. 6 is a close up view of an example of a feedback member at the proximal end of the hollow body.

FIG. 6 shows an example of the feedback member 120 at the proximal end 106 of the hollow body 105. The feedback member 120 provides tactile feedback to the surgeon. The feedback member 120 has a first surface and second surface, some of which may be held by the surgeon. In use, some examples of the feedback member 120 are held between the surgeon's thumb and forefinger. Other examples of the feedback member 120 are held in the surgeon's palm.

Some examples of the feedback member 120 have an asymmetrical shape. The asymmetrical shape of the feedback member 120 has a plane of asymmetry 150 orthogonal to a longitudinal plane containing the leading edge 145. (The leading edge 145 is described above with reference to FIG. 4.) The asymmetrical shape indicates to the surgeon a rotational orientation of the bevel 115.

As the surgeon uses the surgical needle 100 and rotates the feedback member 120, the asymmetrical shape of the feedback member 120 gives the surgeon instant feedback on the rotation. The asymmetrical shape of the feedback member 120 gives the feedback member 120 an asymmetrical feel in the surgeon's hand that changes as the surgeon controls the feedback member 120. For example, the surgeon holds the feedback member 120 at a 12 o'clock position and then rotates the feedback member 120 to a 6 o'clock position. In the surgeon's hand, the feedback member 120 at the 12 o'clock position feels different than at the 6 o'clock position. Because of the fixed relationship between the feedback member 120 and bevel 115, any rotation of the feedback member 120 translates into a corresponding rotation of the bevel 115. Thus, the feedback member 120 enables the surgeon to feel the bevel 115 being rotated.

The foregoing feature is particular beneficial when the surgeon attempts, without direct visualization of the bevel 115, to rotate the surgical needle 100 so that bevel 115 is facing the femoral head, for example. This orientation encourages the bevel 115 to deflect away rather than cut/penetrate into the cartilage, and thus avoid iatrogenic damage to the femoral head, for example. And, in turn, reducing the possibility of complications and reducing recovery time from arthroscopic surgery.

The asymmetrical shape of the feedback member 120 can be any number of any shapes having a plane of asymmetry 150 orthogonal to a longitudinal plane containing the leading edge 145. As shown in FIG. 6, an example of the asymmetrical shape includes a beveled surface 150. In a convenient example of the feedback member 120, the beveled surface 150 is roughly parallel to the face 140 of the bevel 115.

Figure 7:
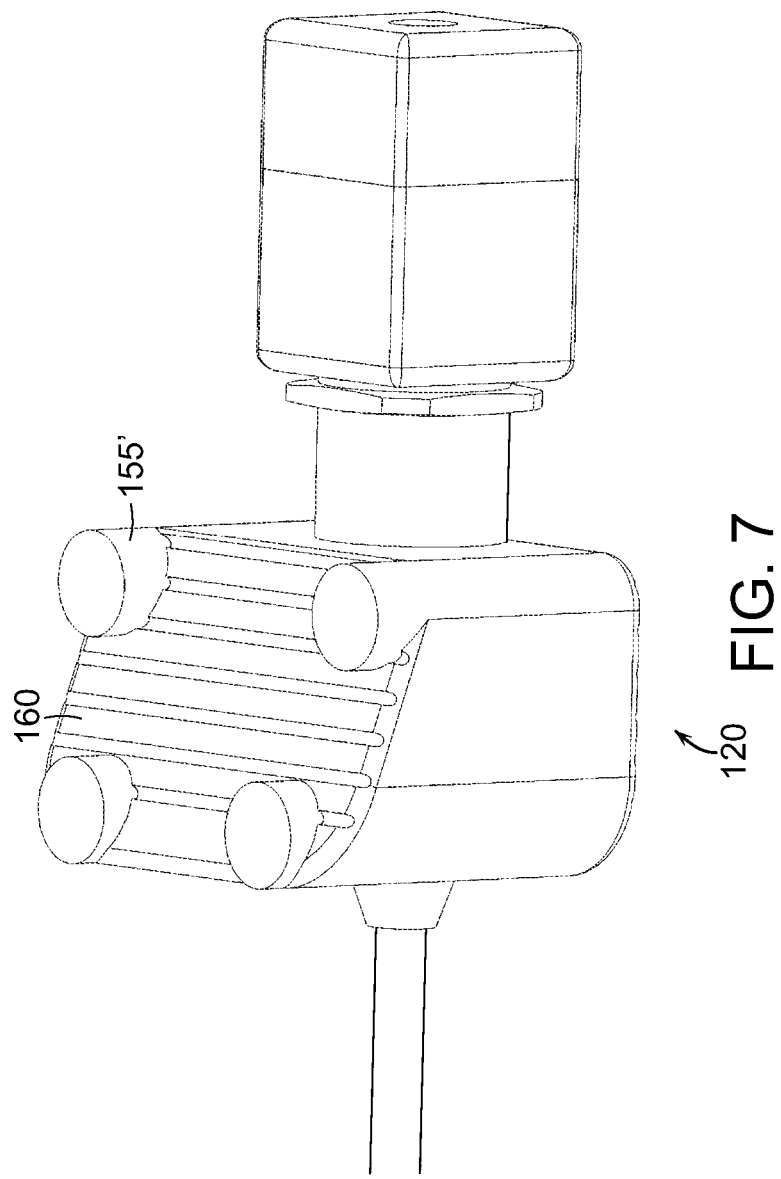
FIG. 7 is a close up view of another example of the feedback member at the proximal end of the hollow body.

FIG. 7 shows another example of the asymmetrical shape. The example has a beveled surface 150' and raised projections 160 extending from the beveled surface 150'. The combination of features heightens the tactile feedback of the feedback member 120. Combinations, such as the one shown in the figure, may be advantageous, especially considering that the surgeon may be feeling the feedback member 120 with their less sensitive palm. The surgeon's sense of touch is further lessened by the additional layer of a glove worn by the surgeon. In addition to raised projections 160, other tactile detectable features are possible, such as a depression, ridge(s), and raised shapes.

Figure 8:
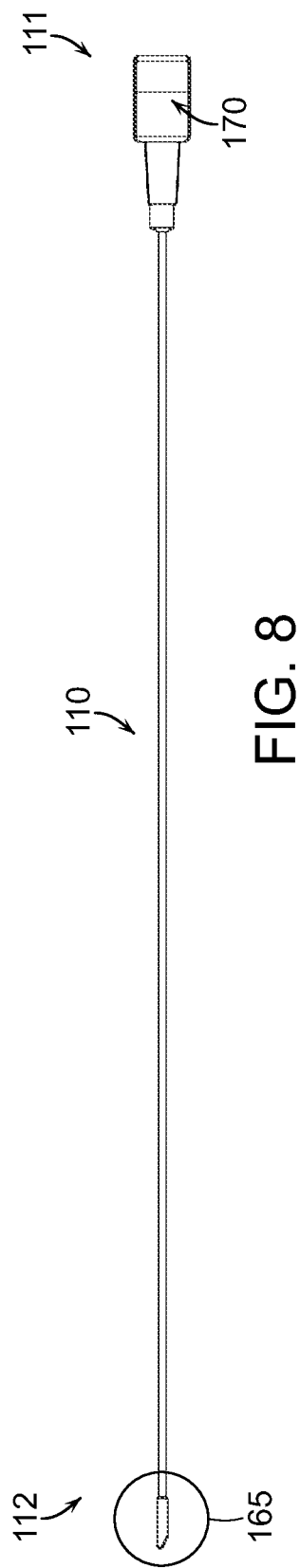
FIG. 8 is a side view of an example of the stylet with a resistance reducing member and stylet hub.

FIG. 8. shows an example of the stylet 110 with a proximal end 111 and distal end 112. At the distal end 112 of the stylet 110 there is a resistance reducing member 165. At the proximal end 111 of the stylet 110 there is a stylet hub 170.

Figure 9A:
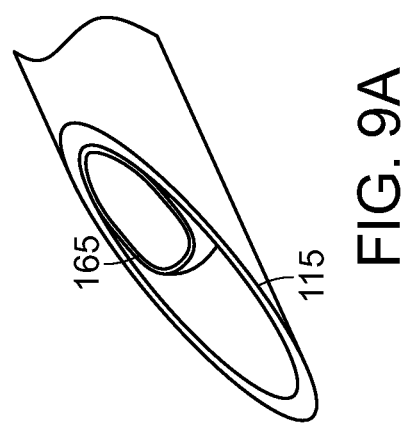

FIGS. 9A and 9B show an example of the resistance reducing member 165. The resistance reducing member 165 has a shape or profile such that when the stylet 110 is in the extended position, the resistance reducing member 165 is in front of the tip 130 of the bevel 115 and protects the tissue from being cut/penetrated by the tip 130. When the stylet 110 is in the retracted position, the resistance reducing member 165 is located at a predetermined position relative to the bevel 115 of the hollow body 105. In this position, the resistance reducing member 165 reduces resistance of the surgical needle 100 through the tissue. The resistance is less than the resistance of a surgical needle with an opened end that allows tissue to enter as the surgical needle is being pushed through the tissue. In a convenient example, the resistance reducing member 165 has a spherical portion 175 and planar portion 180. The spherical portion 175 minimizes or prevents trauma to delicate structures. The planar portion 180 reduces resistance through tissue.

Returning to FIG. 8, the stylet hub 170 is disposed at the proximal end 111 of the stylet 110. The stylet hub 170 together with the opening 125 and passageway 127 of the feedback member 120 serve to couple the stylet 110 and hollow body 105 together (best seen in FIG. 3). The stylet hub 170 has a geometry (shape, size, length, etc.) suitable for being held in the surgeon's palm.

Figure 10:
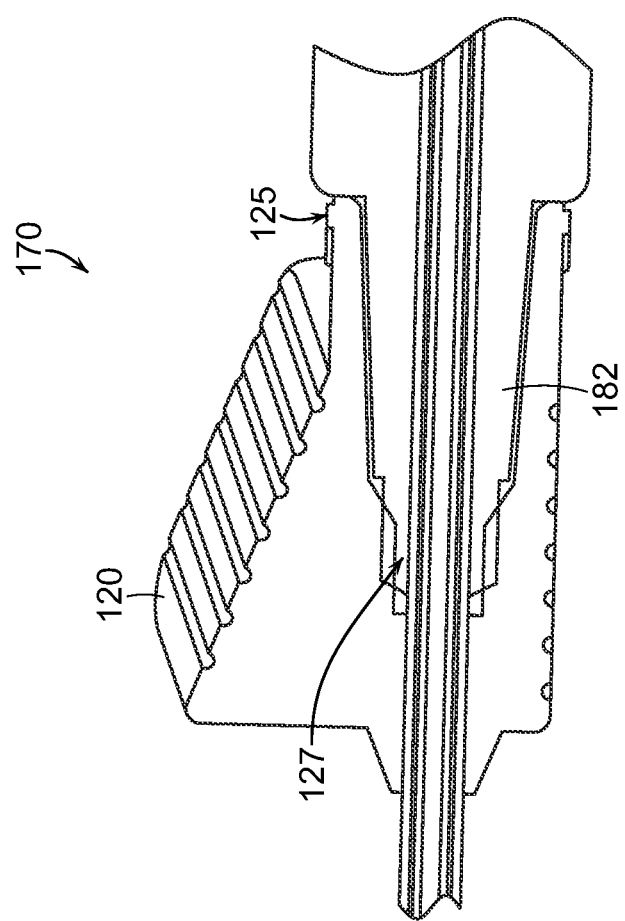
FIG. 10 is a close up view of an example of the surgical needle with a locking member.

FIG. 10 shows the proximal end 102 of an example of the surgical needle 100 in which the hollow body 105 and stylet 110 are detachably coupled to one another. In this example, the stylet hub 170 includes a locking member 182 configured to couple the hollow body 105 and stylet through the opening 125 and passageway 127 of the feedback member 120. To join (or assemble) the hollow body 105 and stylet 110, the distal end 112 of the stylet 110 is inserted into the opening 125 of the feedback member 120 at the proximal end 106 of the hollow body 105. The stylet 110 is then slid through the passageway 127 and through the interior of the hollow body 105 until the feedback member 120 and stylet hub 170 meet.

Convenient examples of the locking member 182 and passageway 127 have mating threads. The locking member 182 is screwed into the feedback number, securing the hollow body 105 and stylet 110 together as the surgical needle 100. To unjoin (or disassemble) the hollow body 105 and stylet 110, the foregoing procedure is done in reverse. In addition to mating threads, other internal features are possible, such as friction or snap fits. In other examples of the surgical needle 100, the locking member 182 and passageway 127 include an external feature to detachably couple the hollow body 105 and stylet 110 together, such as luer-lock.

The foregoing examples of the surgical needle 100 may be assembled or disassembled quickly and easily. These examples advantageously enable the hollow body 105 and stylet 110 to be in a predetermined, closest proximity such that the relationship of the bevel 115 and resistance reducing member 165 is repeatable leading to consistent and predictable results, for example.

Figure 11A:
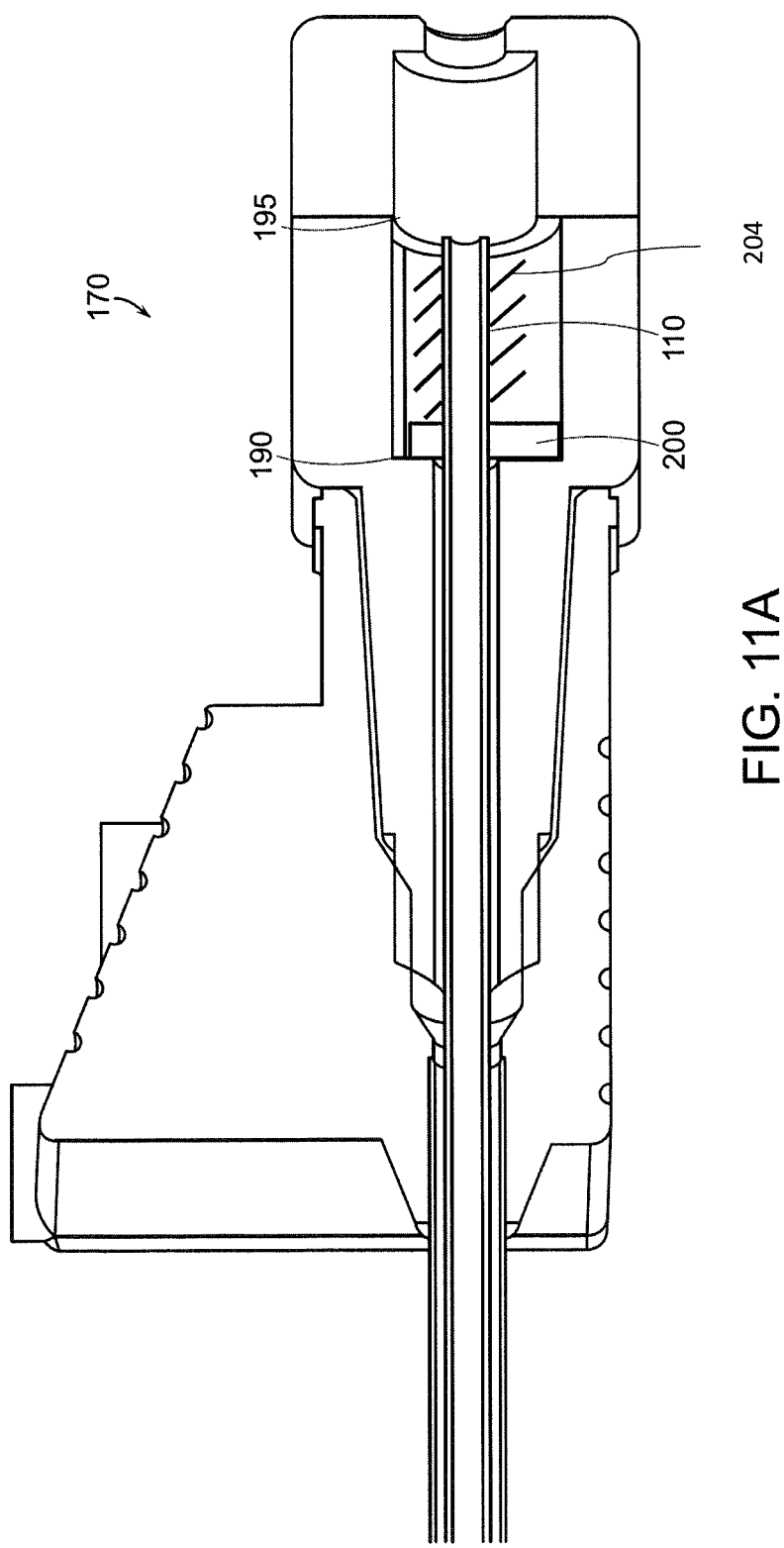
FIGS. 11A-C are close up views of an example of the stylet hub with a proximal stop.
Figure 11B:
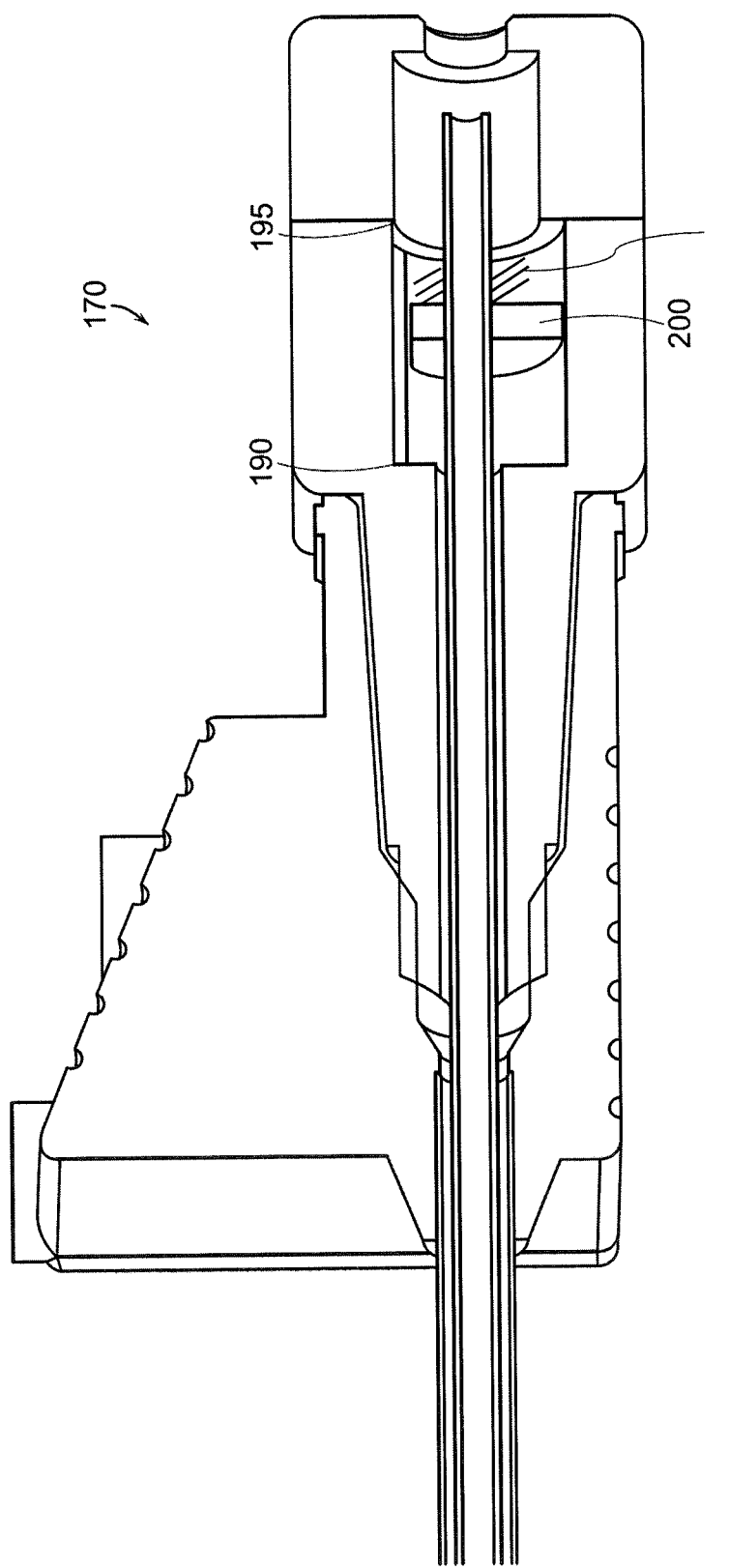
Figure 11C:
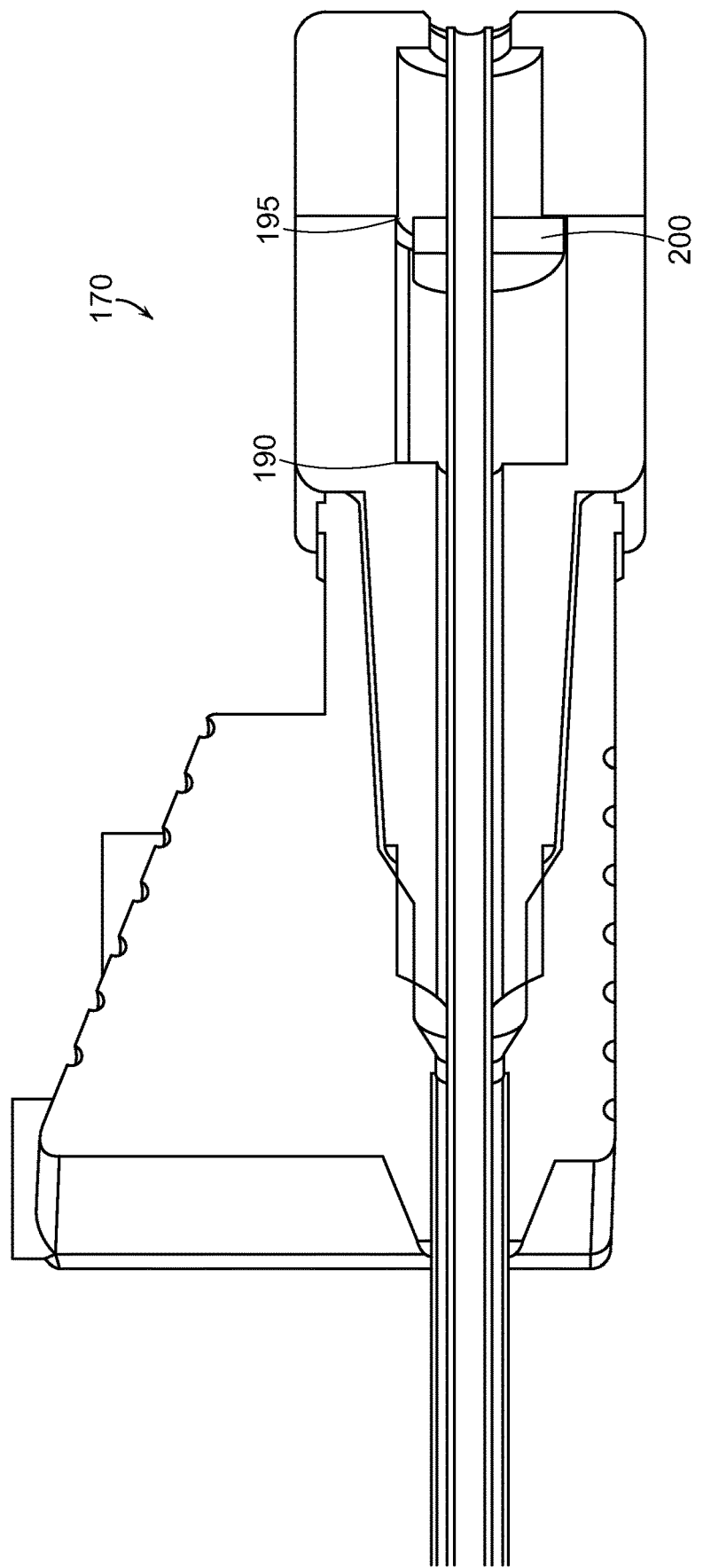

FIG. 11A-C show an example of the stylet hub 170 configured to allow the resistance reducing member 165 to move a preset distance relative to the bevel 115 of the hollow body 105, so as to reduce resistance of the surgical needle 100 through tissue. The stylet hub 170 includes a distal hard stop 190 that defines the extended position of the stylet 110 and a proximal hard stop 195 that defines the retracted position of the stylet 110. A stop 200 fixed to the stylet 110 moves between the distal hard stop 190 and proximal hard stop 195. Because the stop 200 is fixed to the stylet 110, the stylet 110 also moves between the distal hard stop 190 and proximal hard stop 195. An advantage to this hub configuration is that the proximal hard stop 195 prevents retrograde movement of the stylet 110 at a predetermined position relative to the bevel 115, so that the best resistance reducing geometry can be obtained.

The stylet hub 170 further includes a biasing means 204 for urging the stop 200 against the distal hard stop 190. The biasing means 204 also counters a force of the tissue being pushed against the stylet 110, referred to as "tissue force," as the surgical needle 100 moves through the tissue. In the absence of a sufficient tissue force, a biasing force from the biasing means 204 acts on the stylet 110 to push the stylet 110 distally into a fully or partially extended position. FIG. 11A shows the initial position in which the stop 200 is biased distally against the distal hard stop 190 and the stylet 110 is the fully extended position. FIG. 11B shows the stop 200 in mid stroke, touching neither distal nor proximal stops; and the stylet 110 is the partially extended position.

When the tissue force is larger than the biasing force, the stylet 110 retracts. FIG. 11C shows the stop 200 against the proximal hard stop 195 and the stylet 110 in the retracted position. Because the stylet 110 is rigidly attached to the stop 200 and the proximal hard stop 195 prevents the retrograde movement of the stop 200, the stylet 110 cannot move further back. As such, another advantage to this example of the stylet hub 170 is that best resistance reducing geometry is maintained even when the tissue force is further increased (e.g., entering denser tissue). The foregoing feature may be beneficial to procedures in which the surgical needle 100 crosses several tissue layers each of differing "toughness."

In a convenient example of the stylet hub 170, the stop 200 has a flat top to rotationally key the resistance reducing member relative to the bevel 115. This arrangement is beneficial because the relationship of the resistance reducing member and bevel 115 is repeatable, leading to consistent and predictable results.

As the surgical needle 100 is driven through tissue towards a joint, the surgical needle 100 eventually exits the tissue and thus, the force of tissue acting against the stylet 110 is no longer present. Without this force, the stylet 110 springs forward thus shielding the tip 130 from touching delicate joint structures, such as cartilage.

Figure 12A:
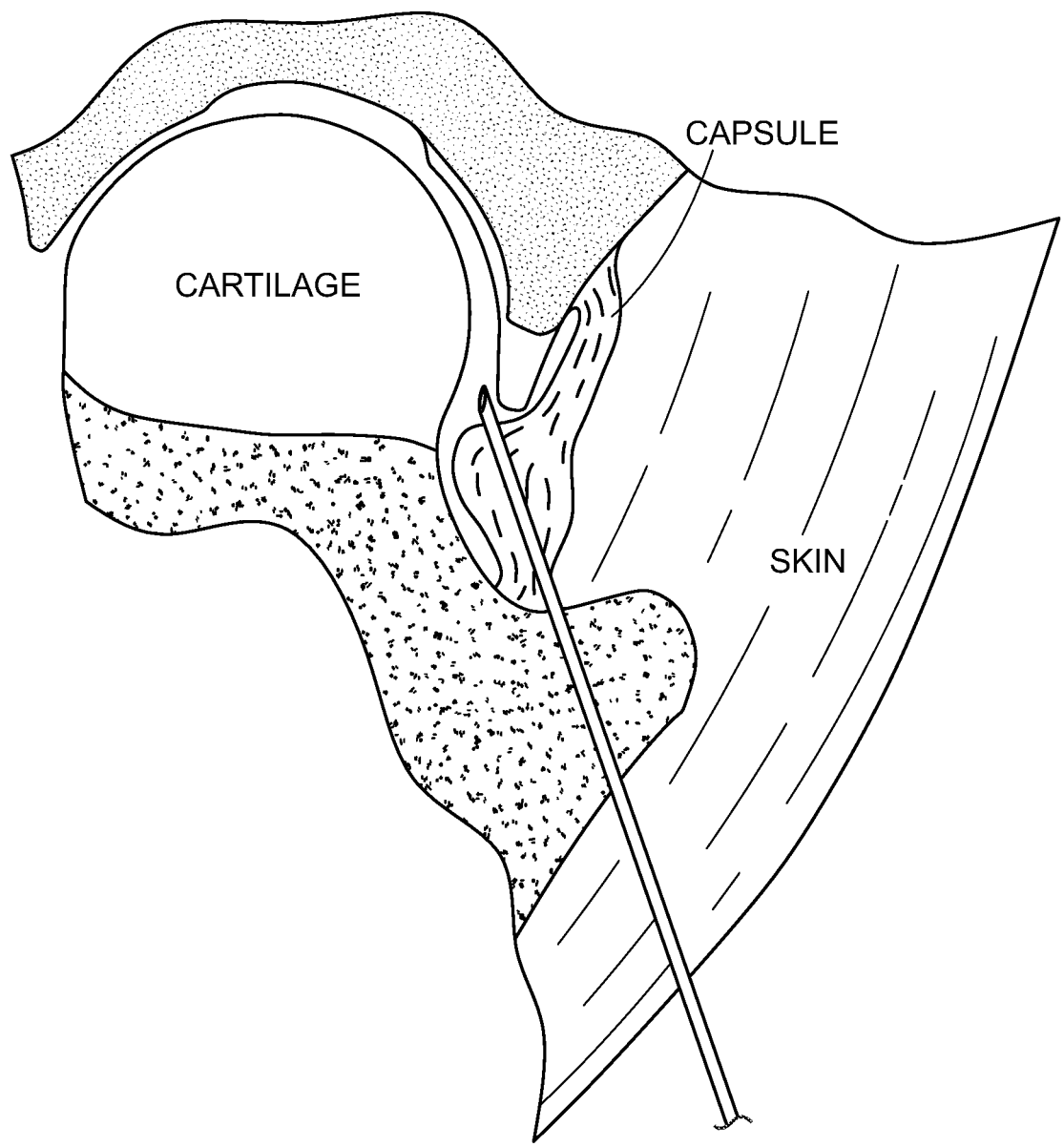
FIGS. 12A and 12B are views of trajectories of a surgical needle into a hip joint.
Figure 12B:
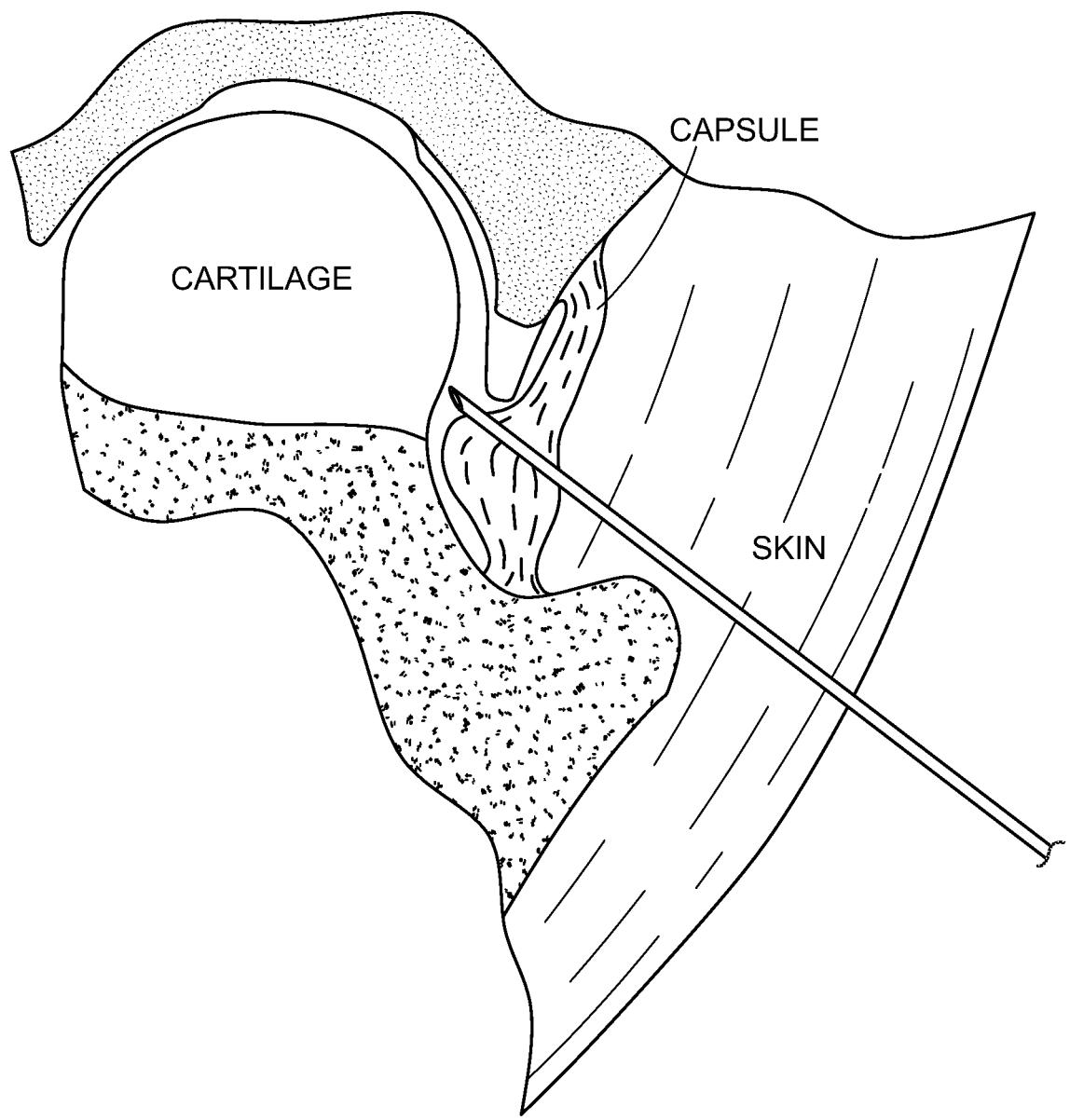

When the surgical needle 100 enters a joint at a tangential trajectory, the sprung stylet 110 does not encounter a force to push the stylet 110 back (shown in FIG. 12A). When the surgical needle 100 enters a joint in a more perpendicular trajectory, the sprung stylet 110 does encounter a force to push the stylet 110 back, thus exposing the tip 130 to joint structures, such as the femoral head cartilage in the hip joint (shown in FIG. 12B). In this situation, it is desirable to have the stylet 110 lock in its furthest distal (extended) position after the stylet 110 has sprung forward, thus preventing the stylet 110 from exposing the tip 130.

Figure 13B:
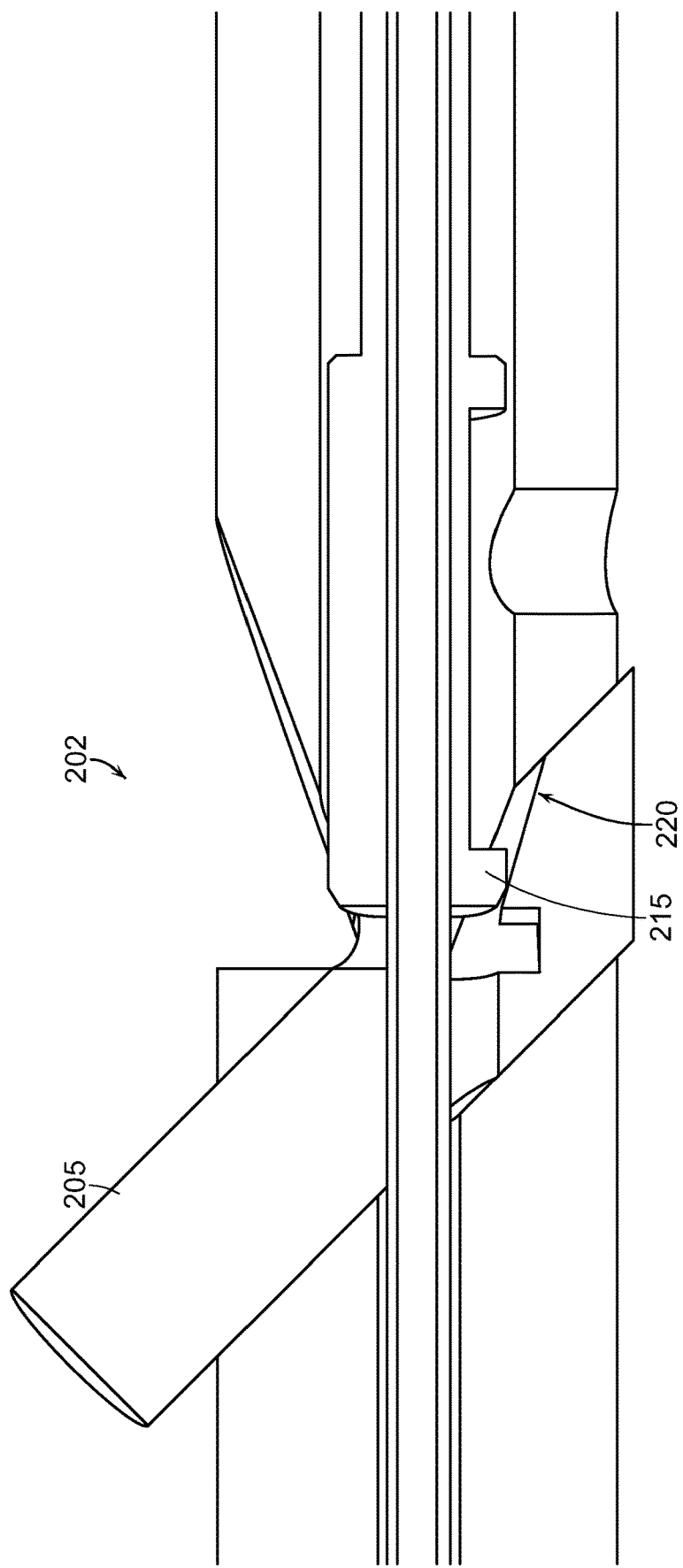
Figure 13C:
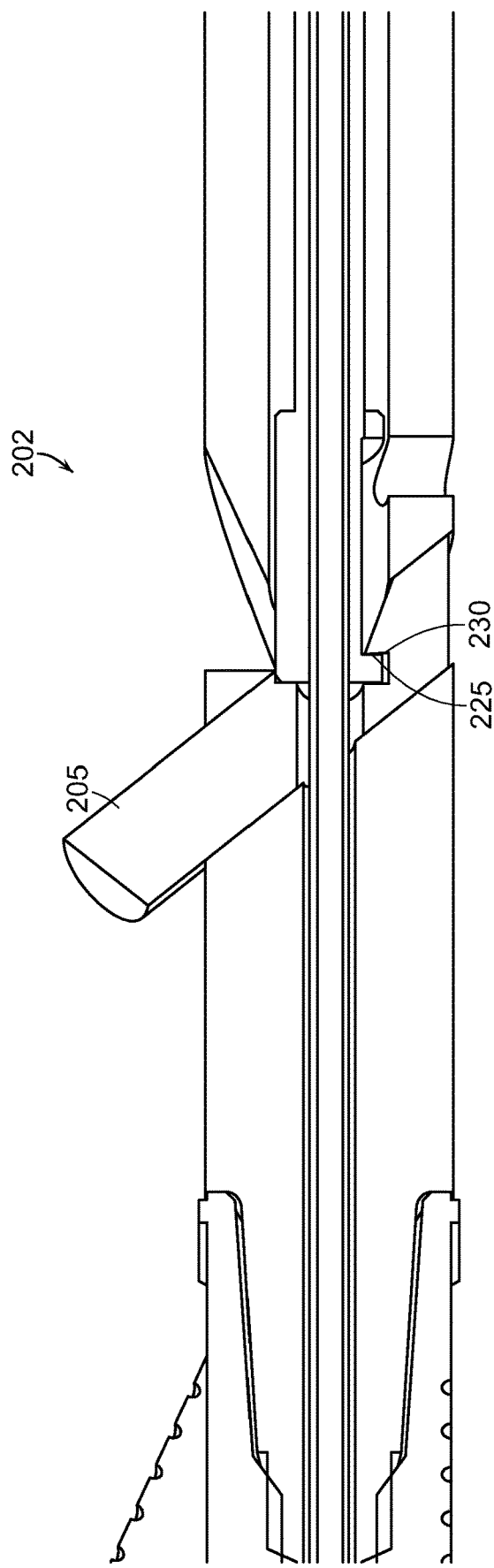

FIGS. 13A-C shows an example of the stylet hub 170 with a stylet locking member 202. The stylet locking member 202 locks the stylet 110 in the extended (non-cutting/non-penetrating) position, automatically, and prevents the stylet 110 from sliding back to the retracted (cutting/penetrating) position behind the tip 130. The example of the stylet locking member 202 shown in FIG. 13A includes a lock/unlock button 205. The lock/unlock button 205 is allowed to slidably move in a bore set 210 at an angle to the stylet 110.

When the stylet 110 no longer sees a retraction force (e.g., force of tissue acting against the stylet 110) the stylet 110 moves distally causing an integral feature 215 in the hub area to hit an inclined surface 220 on the lock/unlock button 205, as shown FIG. 13B. This in turn drives the lock/unlock button 205 downwards, allowing a locking lip 225 on the lock/unlock button 205 to engage with a corresponding locking lip 230, as shown FIG. 13C. As the lock/unlock button 205 is biased (e.g., by a spring), the lock/unlock button 205 forces the locking lips 225, 230 to engage and prevents the stylet 110 from moving in the proximal direction.

The stylet locking member 202 is particular advantageous when there is only a small space or gap between the exit side of the tissue being pierced by the surgical needle 100 and delicate structures, such as vessels and nerves. When operating in such a tight space, it is very easy to "pop" through the tissue and cut/penetrate these delicate structures with the surgical needle 100. Locking the stylet 110 in the extended (non-cutting/non-penetrating) position, automatically, as the surgical needle 100 exits the tissue prevents the surgical needle 100 from further cutting/penetrating and causing damage, inadvertently.

In practice, however, the surgical needle 100 is often "pistoned" in and out as the surgeon directs the trajectory of the surgical needle 100 towards the joint. Because stylet retraction depends on a tissue force pushing the stylet 110 proximally, this pistoning causes the stylet 110 to spring distally every time the surgeon pulls the surgical needle 100, proximally. In a convenient example, the locked stylet 110 is easily unlocked by the surgeon in order to minimize surgical time. Some examples of an unlock feature having various geometries are provided below.

In the example shown in the FIGS. 13A-C, the lock/unlock button 205 is easily unlocked by the surgeon's thumb, which is naturally on the feedback member 120 next to the unlock button. The surgeon depresses the lock/unlock button 205 to separate the locking lips 225, 230 and allow the stylet 110 to retract in the proximal direction. This geometry is particularly convenient when the stylet hub 170 is positioned in the surgeon's palm with their thumb and forefinger providing control on the feedback member 120.

Figure 14A:
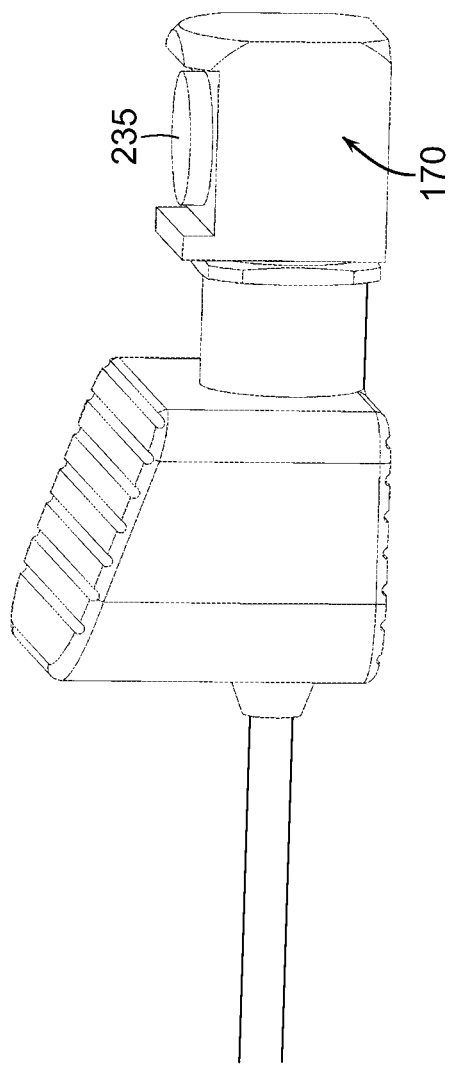

FIG. 14A shows another example of the stylet locking member 202 with an unlock button 235. The arrangement shown is particularly convenient when the stylet hub 170 is positioned with the surgeon's thumb and forefinger providing control on the feedback member 120.

FIG. 14B shows yet another example of the stylet locking member 202 with a unlock lever 240. The arrangement shown is particularly convenient when the surgeon holds the feedback member 120 in the surgeon's palm and hollow body 105 between their thumb and forefinger. The unlock lever 140 is within easy reach of the surgeon's fingers without them repositioning.

FIGS. 15A-F show an example procedure for entering a joint space through tissue using an example of the surgical needle 100 described above. Each of the figures includes a close up view of the distal end 101 of the surgical needle 100. Of particular note is correspondence between position the stylet 110 and progress of the surgical needle 100.

Figure 15A:
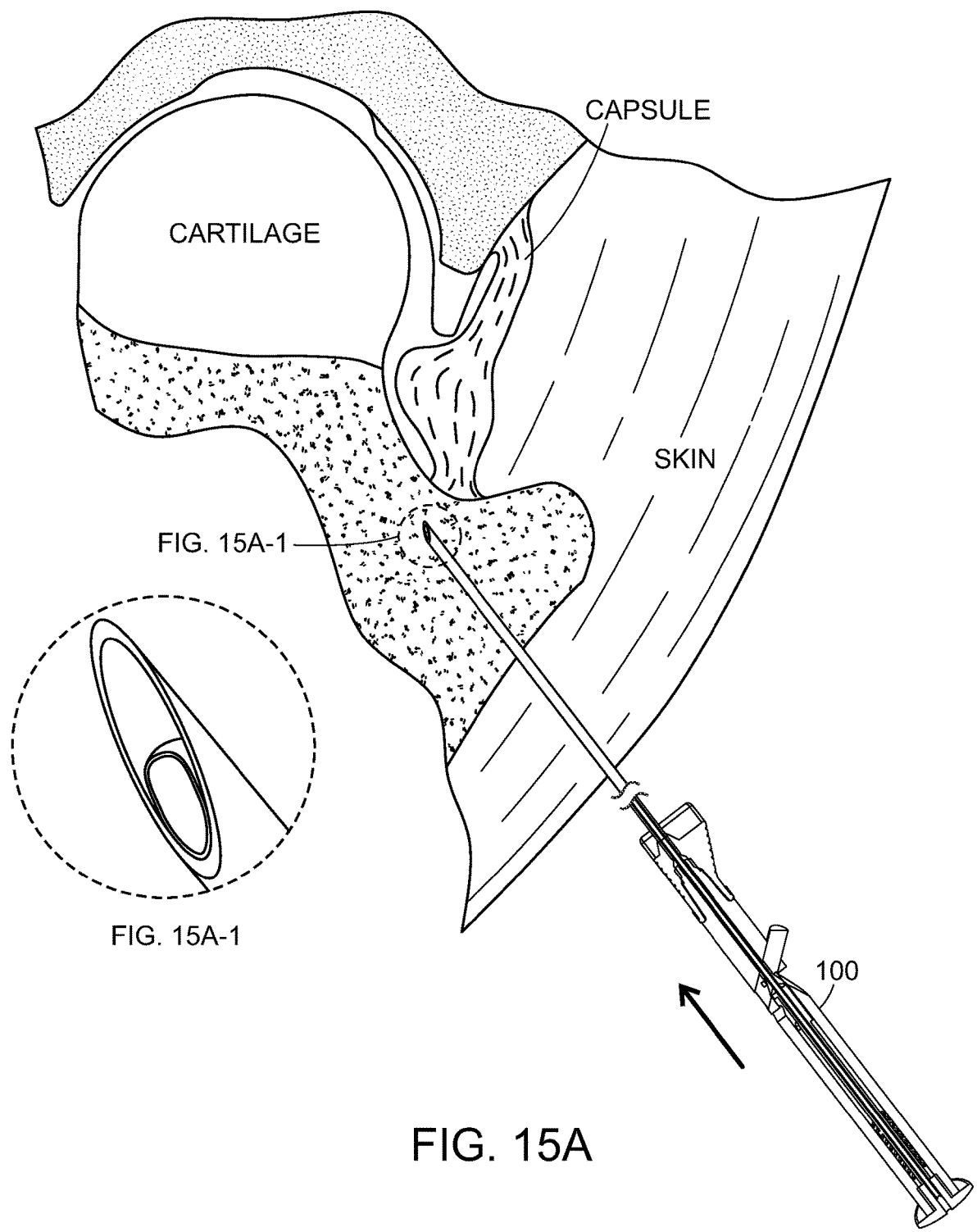
FIGS. 15A-F are views of a procedure for entering a joint space through tissue using an example of the surgical needle.

FIG. 15A shows the surgeon pushing the surgical needle 100 through tissue along an initial trajectory. The stylet 110 is retracted exposing the cutting/penetrating tip 130 to the tissue. The resistance reducing member 165 is located at a predetermined position relative to the bevel 115 of the hollow body 105. The surgeon uses less force to push the surgical needle 100 through the tissue because the resistance is reduced. The initial trajectory, however, is wrong and the surgical needle 100 will miss the capsule.

Figures 1, 15B:
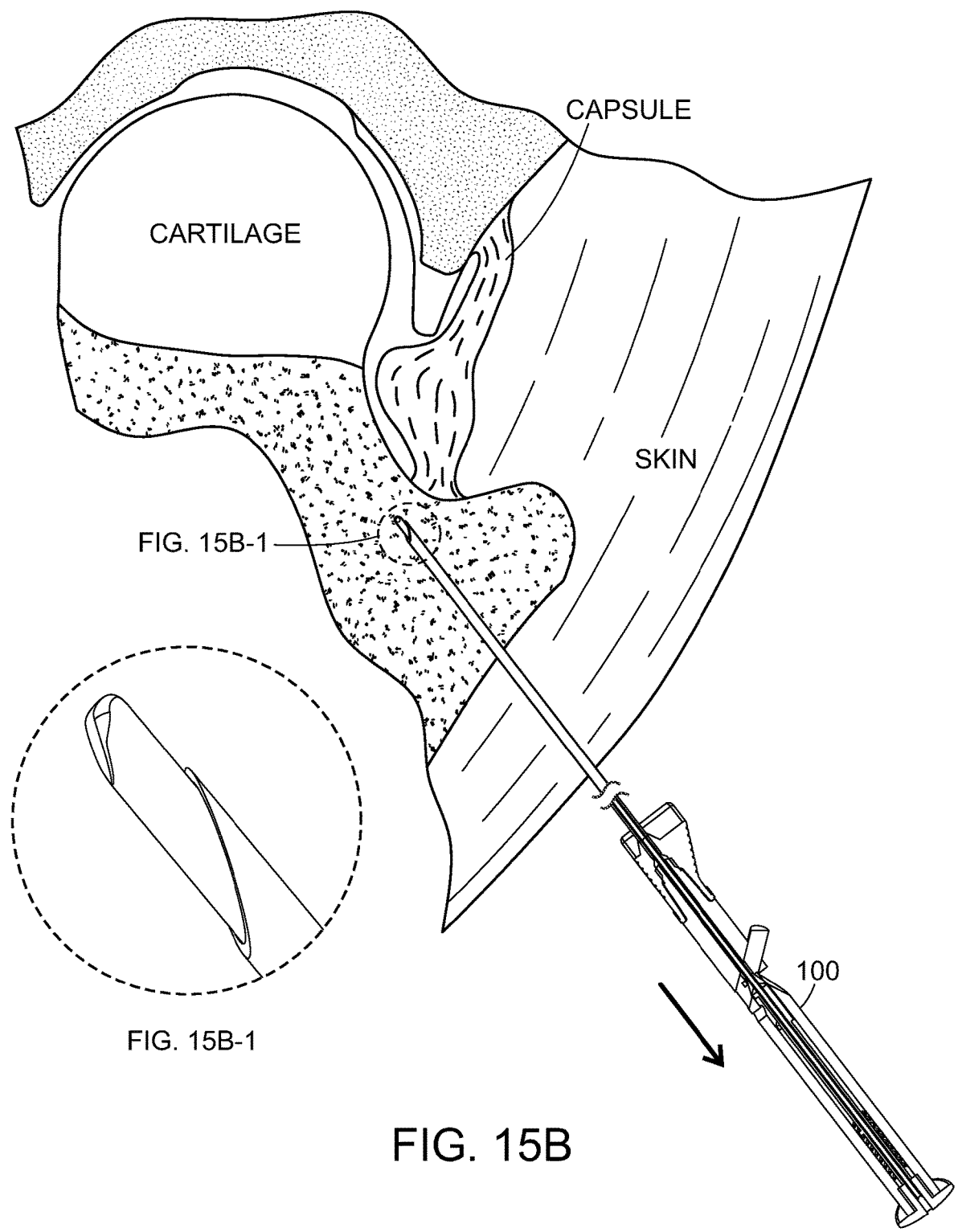

FIG. 15B shows the surgeon pulling the surgical needle 100 back. In the absence of tissue pushing against the stylet 110, the stylet 110 extends. Extension of stylet 110 causes the stylet locking member 202 to lock the stylet 110 in the extended position, automatically.

Figures 1, 15C:
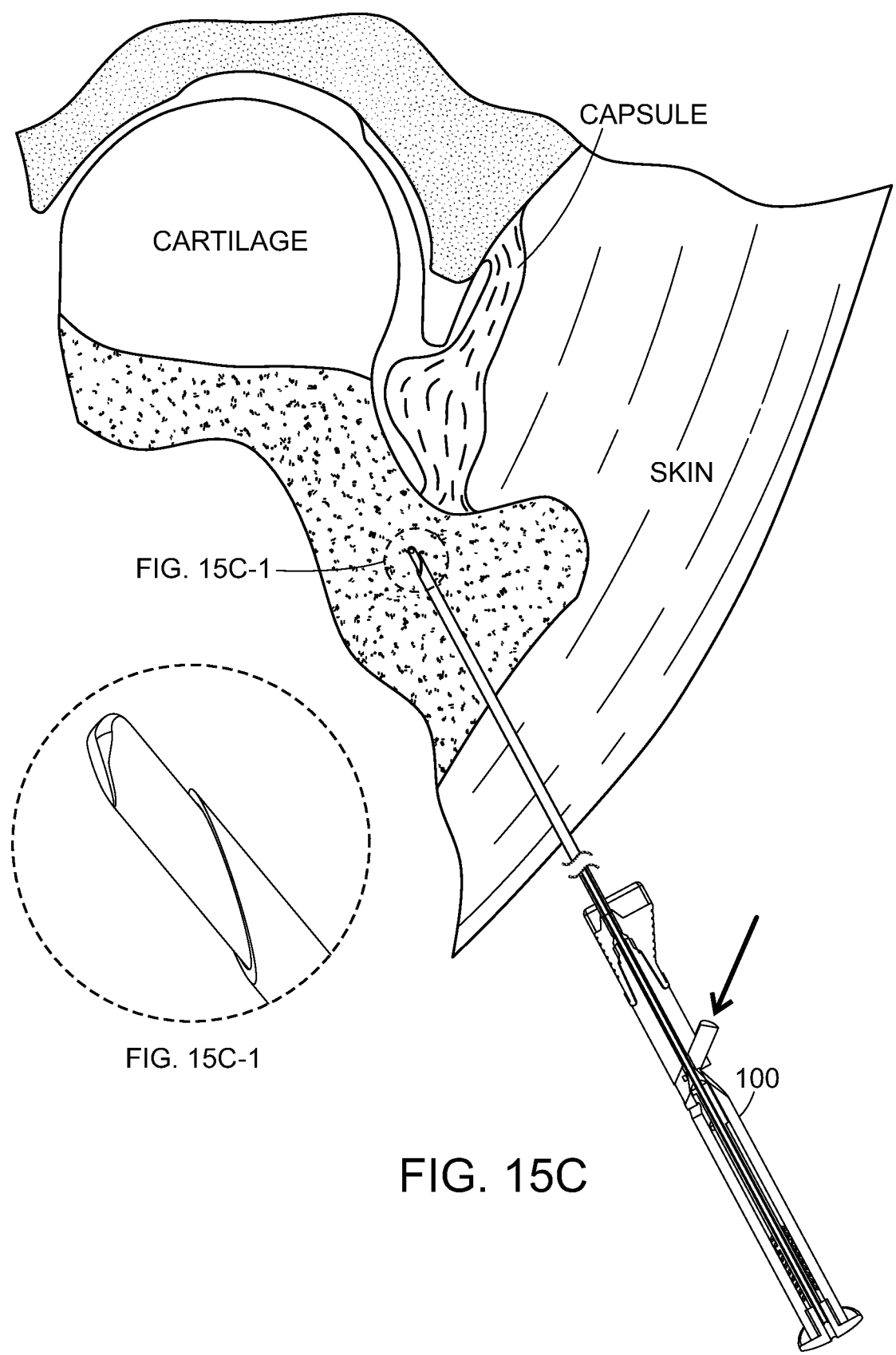

FIG. 15C shows the surgeon depressing the lock/unlock button 205 of the stylet locking member 202 to unlock the locked stylet 110 from the extended position, manually.

Figure 15D:
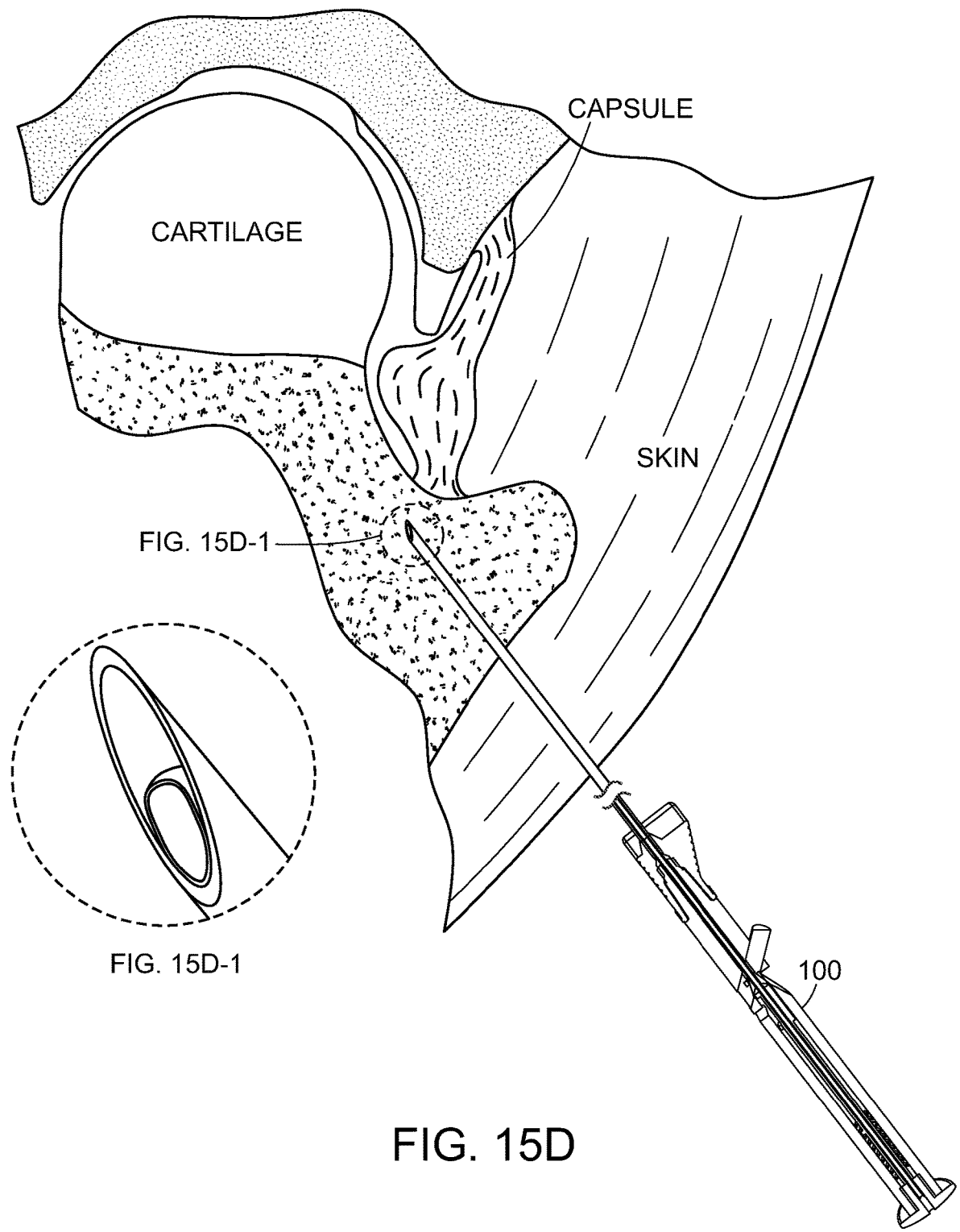

FIG. 15D shows the surgeon redirecting the surgical needle 100 with the stylet 110 in retracted position and the cutting/penetrating tip 130 exposed. The surgeon may repeat the foregoing steps (pushing, pulling, unlocking) several times during the procedure. This is referred to as "pistoning."

Figure 15E:
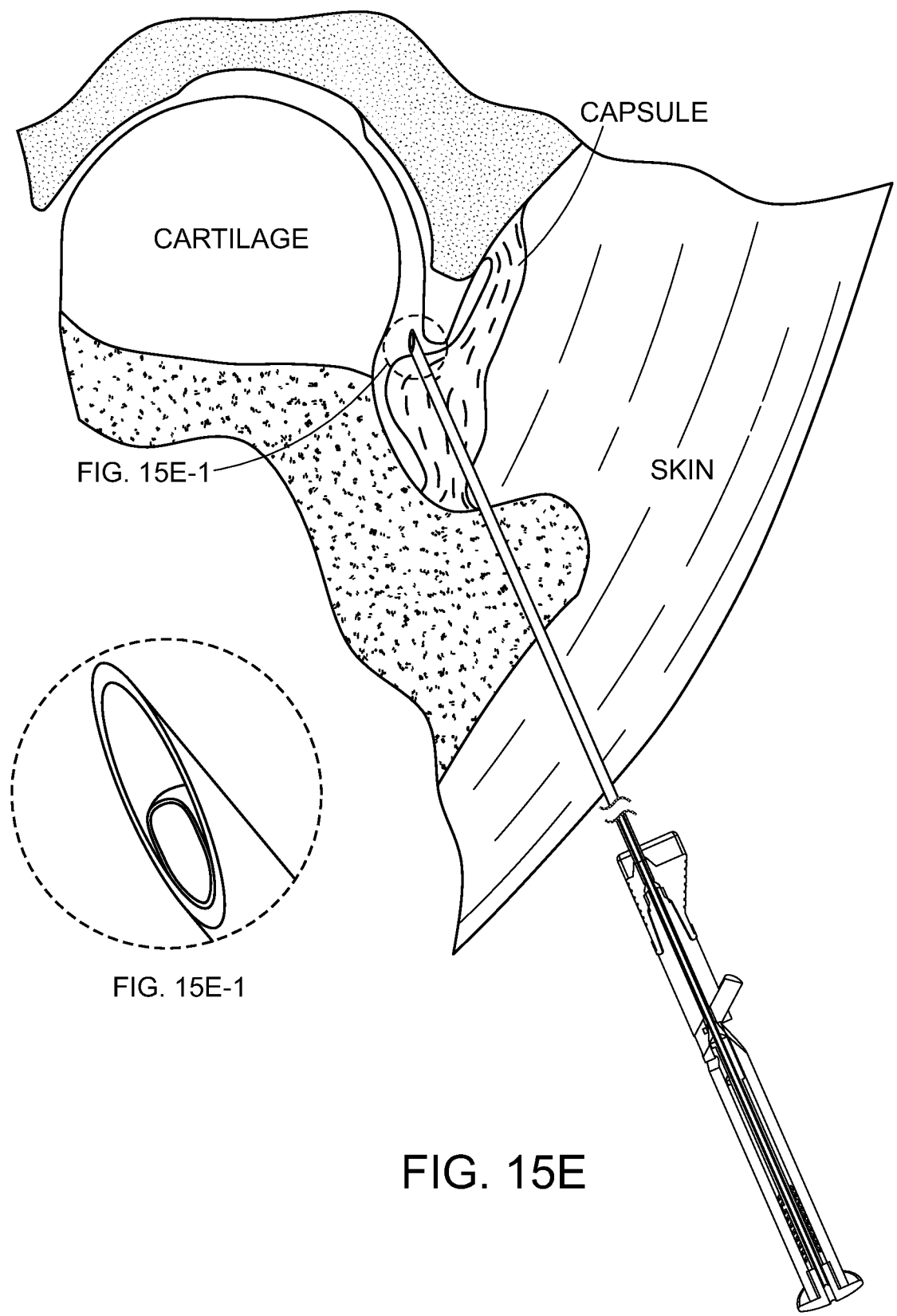

FIG. 15E shows the surgeon pushing the surgical needle 100 through the capsule. The stylet 110 is the retracted position, the cutting/penetrating tip 130 exposed, and the resistance reducing member 165 is located at the predetermined position relative to the bevel 115 of the hollow body 105. The femoral head with delicate cartilage is very close to where the bevel 115 is about to exit the capsule, completely.

Figures 1, 15F:
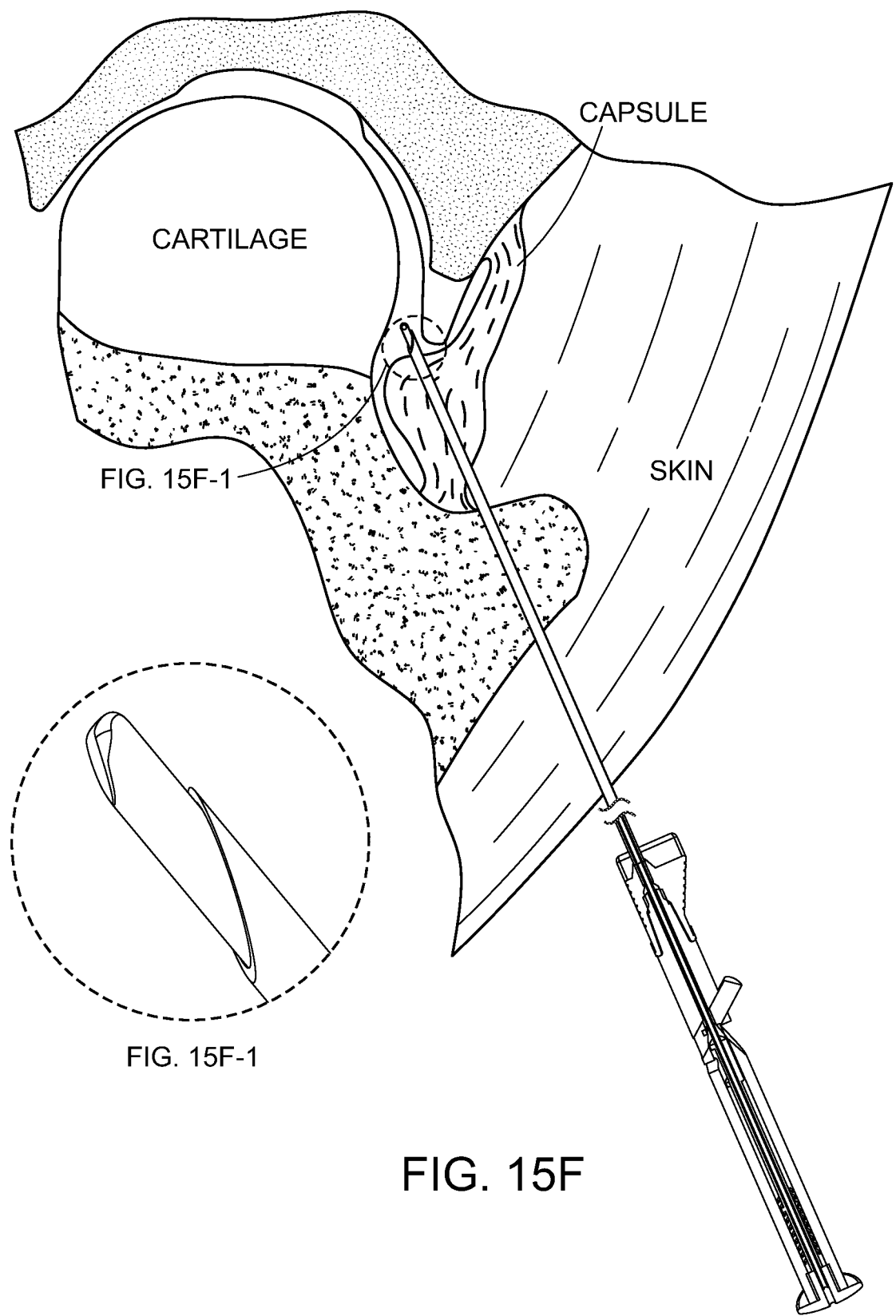

FIG. 15F shows the surgeon pushing surgical needle 100 so that that the bevel 115 is completely through the capsule and in the joint space. In the absence of tissue pushing against the stylet 110, the stylet 110 extends. Extension of stylet 110 causes the stylet locking member 202 to lock the stylet 110 in the extended position, automatically. Should the surgeon continue pushing the surgical needle 100, the locked stylet 110 minimizes or prevents damage to the femoral head.

In the foregoing example, the joint space is the hip joint. The hip example is but one example and is not limiting. Procedures for entering other joint spaces, such as the shoulder or ankle, are similar.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described examples, but should be defined only in accordance with the following claims appended hereto and their equivalents.

What is claimed is:

1. A surgical needle for entering a joint space through tissue, the surgical needle comprising:
   a hollow body having a distal end and proximal end, a bevel disposed at the distal end of the hollow body, and a tip at a distal most end of the bevel, the bevel having a face extending between the tip and a proximal most end of the bevel;
   a feedback member coupled to the proximal end of the hollow body, a passageway within the feedback member defined by an opening at one end of the feedback member, the passageway being in communication with an interior of the hollow body;
   a stylet having a distal end and proximal end, the stylet movable within the hollow body between an extended position and retracted position;
   a resistance reducing member disposed at the distal end of the stylet, the resistance reducing member shaped as a partial sphere with a planar side extending parallel with the bevel of the hollow body, the resistance reducing member being forward of the tip of the bevel when the stylet is in the extended position, and located at a predetermined position relative to the bevel when the stylet is in the retracted position;

a stylet hub disposed at the proximal end of the stylet, the stylet hub together with the passageway and the opening of the feedback member coupling the stylet and hollow body together, the stylet hub further comprising:

- a stop fixed to the stylet and enclosed within a bore of the stylet hub, a distal end of the bore defining a distal hard stop limiting distal movement of the stop through the bore and a proximal end of the bore defining a proximal hard stop limiting proximal movement of the stop through the bore, the distal hard stop defining the extended position of the stylet and the proximal hard stop defining the retracted position of the stylet; and
- a biasing member positioned at a location proximal to a proximal end of the stop for urging the stop against the distal hard stop; and a locking member, the locking member being separate and distinct from the feedback member, the locking member configured for insertion into the opening of the feedback member for detachably coupling the stylet and the hollow body together, the locking member and passageway of the feedback member include mating threads;

wherein the feedback member has an asymmetrical shape defined by a feature of the feedback member having a fixed relationship with the orientation of the bevel, the fixed relationship indicating to a user a rotational orientation of the bevel through tactile feedback when the user rotates the feedback member 180 degrees;

wherein the feature of the feedback member includes a beveled first surface extending from a distal end to a proximal end of the feedback member such that a direction of the extension is toward a longitudinal plane, and a non-beveled second surface opposite the first surface extending along the longitudinal plane from the distal end to the proximal end of the feedback member; and wherein the face of the bevel of the hollow body faces in a first direction when the beveled first surface of the feedback member is facing in a second direction opposite the first direction.

2. The surgical needle of claim 1 wherein the face of the bevel and the beveled first surface of the feature of the feedback member are substantially parallel.

3. The surgical needle of claim 1 wherein the beveled first surface of the feature of the feedback member includes tactile detectable features.

4. The surgical needle of claim 1 wherein the stylet hub includes a stylet locking member locking the stylet in the extended position, automatically, in the absence of tissue force acting against the stylet.

5. The surgical needle of claim 4 wherein the stylet locking member includes a lock/unlock button slidably moveable within a bore set at an angle to the stylet.

6. The surgical needle of claim 1 wherein the stop fixed to the stylet has a flat top to limit rotation of the resistance reducing member relative to the bevel of the hollow body.

7. The surgical needle of claim 1, wherein the stop fixed to the stylet is entirely disposed within the bore of the stylet hub such that no portion of the stop extends from the bore.

8. The surgical needle of claim 1, wherein the proximal hard stop is configured to prevent proximal movement of the stylet at a predetermined position relative to the bevel.

* * * * *